United States Patent [19]

Ciccarelli

[11] Patent Number: 4,691,719
[45] Date of Patent: Sep. 8, 1987

[54] DENTAL FLOSS APPLICATOR

[76] Inventor: Angelo Ciccarelli, 32 N. Osprey Ave., Sarasota, Fla. 33577

[21] Appl. No.: 845,849

[22] Filed: Mar. 28, 1986

[51] Int. Cl.$^4$ ............................................. A61C 15/00
[52] U.S. Cl. ................................ 132/92 R; 132/92 A
[58] Field of Search ............... 132/89, 91, 92 R, 92 A, 132/93

[56] References Cited

U.S. PATENT DOCUMENTS

| | | | |
|---|---|---|---|
| 741,556 | 10/1903 | Sessums | 223/103 |
| 1,205,732 | 11/1916 | Groetchen | 132/92 R |
| 2,467,221 | 4/1949 | Pastl | 132/92 R |
| 3,693,638 | 9/1972 | Ciccarelli | 132/91 |
| 3,847,167 | 11/1974 | Brien | 132/92 R |
| 3,882,879 | 5/1975 | Lucas | 132/92 R |
| 3,885,579 | 5/1975 | Navrat | 132/92 R |
| 3,903,907 | 9/1975 | Knaus | 132/92 R |
| 3,908,678 | 9/1975 | Conn et al. | 132/92 R |
| 3,915,178 | 10/1975 | Zellers | 132/92 R |
| 3,993,085 | 11/1975 | Skinner | 132/92 A |
| 4,064,883 | 12/1977 | Oldham | 132/93 |

Primary Examiner—John J. Wilson
Assistant Examiner—Adriene J. Lepiane
Attorney, Agent, or Firm—Charles J. Prescott

[57] ABSTRACT

A dental floss holder including an elongated body having a pair of opposing, extending forks at one end and a refillable dental floss container at the other end. A floss lock bar is pivotally connected at one end to the midportion of the top surface of the body about a hinge which is mounted transversely in the body of the holder. Each fork has an eyelet connected at its distal end for receiving the dental floss. The floss lock bar is releasably lockable in a closed position against the top surface of the body such that a mating rib and cavity contours therebetween both tension and secure the dental floss fed from the dental floss container to and stretched between each fork eyelet for use and back through the dental floss container for cutting. A separate floss feeder is also provided to facilitate routing the dental floss back through the dental floss container.

6 Claims, 5 Drawing Figures

DENTAL FLOSS APPLICATOR

BACKGROUND OF THE INVENTION

This invention relates generally to apparatus for cleaning the areas between teeth, and more particularly to an improved dental floss applicator with improved structure and functioning for both tensioning, retaining and using the applicator in a position suitable for its intended use.

In my previous U.S. Pat. No. 3,693,638, I disclosed a simpler invention also directed to the retention of a span of dental floss for use. However, that invention, in part because of its simplistic structure, proved less than commercially successful.

Other devices have been disclosed in prior art as set forth in a separate Prior Art Disclosure and need not be discussed here.

Although prior art discloses many previous dental floss applicators with various structures, it is evident by the obvious absence of any such devices in the marketplace that they have proven less than commercially adequate or acceptable.

The present invention is directed to an improved and novel dental floss applicator having both improved structure and function for both tensioning and retaining a length of dental floss provided from a separate refillable dental floss container to and across opposing forks having eyelets in their distal ends and back to the refillable container. Structure in the mid-portion of the main body provides the improved tensioning and locking benefits.

BRIEF SUMMARY OF THE INVENTION

The present invention is that of a dental floss holder including an elongated body having a pair of opposing, extending forks at one end and a refillable dental floss container at the other end. A floss lock bar is pivotedly connected at one end to the mid-portion of the top surface of the body about a hinge which is transverse to the body of the applicator. Each fork has an eyelet connected at its distal end for receiving the dental floss. The floss lock bar is releasably lockable in a closed position against the top surface of the body such that mating rib and cavity contours therebetween both tension and secure the dental floss fed from the dental floss container to and stretched between each fork eyelet for use and back through the dental floss container for cutting. A separate floss feeder is also provided to facilitate routing the dental floss out of and back through the dental floss container.

It is therefore an object of this invention to provide an improved dental floss applicator which includes improved and novel structure for tensioning and securing a length of dental floss.

It is another object to provide the above invention with improved structure and shape for more convenient use.

It is another object to provide the above invention having an easily refillable dental floss container.

In accordance with these and other objects which will become apparent hereinafter, the instant invention will now be described with reference to the accompanying drawings in which:

DETAILED DESCRIPTION OF THE PREFERRED EMBODIMENT

Figure 1:
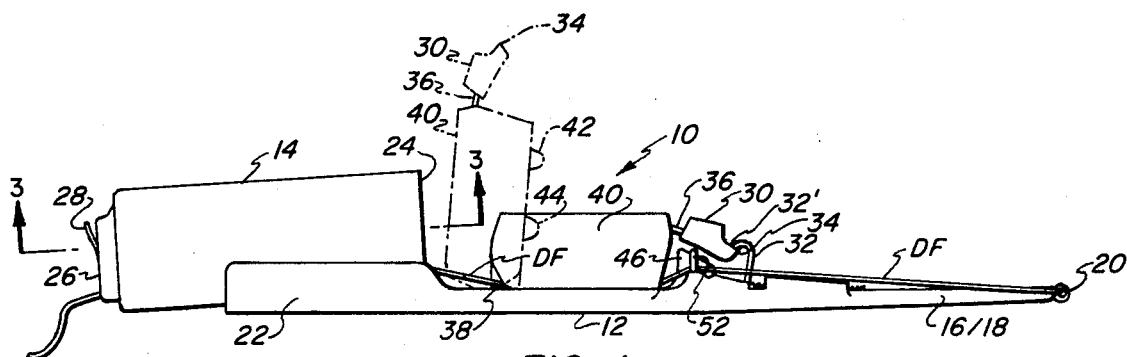
FIG. 1 is a side elevation view of the invention.
Figure 2:
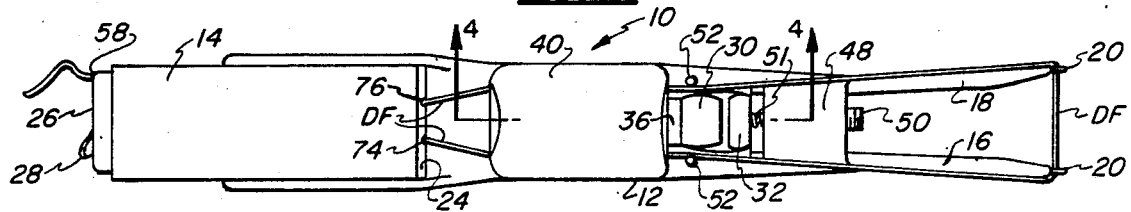
FIG. 2 is a top plan view of the invention.

Referring now to the drawings, and particularly to FIGS. 1 and 2, the invention is shown generally at numeral 10 and includes an elongated body 12, a refillable dental floss container 14 disposed at one end 22 of the elongated body 12, and opposing spaced forks 16 and 18 disposed at the opposite end of the elongated body 12. Pivotedly connected to the elongated body 12 about a transversely disposed hinge 38 is a floss lock bar 40 having a spring catch 30 disposed at the opposite end from the hinge 38. The floss lock bar 40 is shown in phantom in the open position for loading and routing the dental floss DF. The spring catch 30 cooperates with a spring biased release 32 to retain the floss lock bar 40 in the closed position against the top surface of the elongated body 12.

Disposed at the distal ends of the forks 16 and 18 are eyelets 20 which are adapted to supportively receive the dental floss DF. By the space relationship of the forks 16 and 18 and the positioning of the eyelets 20, a span of dental floss thereacross may be provided in tensioned form for use in cleaning between the user's teeth.

Routing of the dental floss DF is from an aperature 74 in the closed end 24 of the dental floss container 14, between the floss lock bar 40 and the mid-portion of the upper surface of elongated body 12, along the top surface of fork 16 and through the eyelet 20 on the distal end of fork 16, and then through eyelet 20 at the distal end of fork 18, back along fork 18's top surface and between floss lock bar 40 and the upper surface of the mid-portion of elongated body 12 and back into the dental floss container 14 through aperature 76. The distal end of the dental floss DF is then pulled out through an aperture 58 in the removeable cap 26 and cut by, and secured to, cutter 28.

Figure 4:
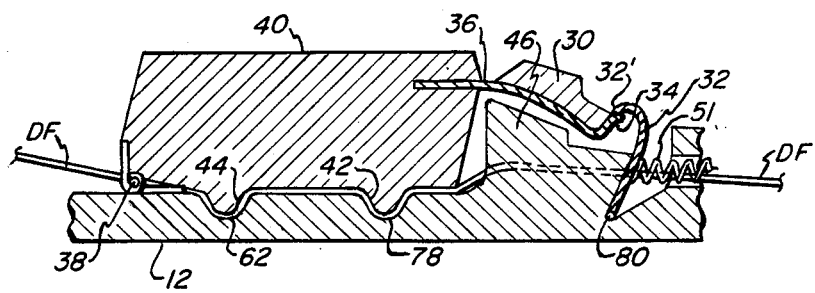
FIG. 4 is a section view through arrows 4—4 in FIG. 2.

After the dental floss DF has been so routed with the floss lock bar 40 in the open, upwardly extending position as shown in phantom, in FIG. 1, the floss lock bar 40 is then pivoted downwardly against the upper surface of the main body 12 and secured thusly by cooperative innerengagement between the spring catch 30 and release 32. Stop 46 prevents excess deforming of metal strip 36 during closure. Referring now also to FIG. 4, the floss lock bar 40 is there shown in the closed and secured position. The floss lock bar 40 includes rib members 42 and 44 which extend in a spaced apart relationship transversely to the floss lock bar 40. Mating transversely disposed cavities 62 and 78 in the top surface of the elongated body 12 receive the ribs 42 and 44 as shown. The ribs 42 and 44 and cavities 62 and 78, as well as the clearance between the bottom surface of floss lock bar 40 and the top surface of the mid-portion of elongated body 12 are adapted to provide minimal but sufficient clearance for the dental floss DF to pass therebetween when the floss lock bar 40 is in the closed and secured position as shown in FIG. 4. An important aspect of this arrangement is that, once the dental floss DF is routed as previously discussed, and secured at its distal end by cutter 28, as floss lock bar 40 is securedly closed, the dental floss DF is tensioned and secured therebetween. This has the beneficial effect of tensioning the span of dental floss between eyelets 20 to improve the usefulness of this invention 10. A spaced pair of upright cylindrical guides 52 serve to prevent the dental floss DF from escaping from between the floss lock bar 40 and cavities 62 and 78.

Still referring to FIG. 4, the spring catch 30 is fabricated of a thin resilient metal strip 36 imbedded into the floss lock bar 40 as shown. The release 32 is fabricated of a thin strip of metal pivotedly mounted at hinge 80 into a recess in the elongated body 12. The release 32 includes a curved portion to provide an interengaging edge 32' which engages over the edge 34 of spring catch 30 as shown. Coil spring 51 provides the spring biased force to releasably maintain this interengagement. By pivoting release 32 away from edge 34, disengagement is effected and floss lock bar 40 may be pivoted upwardly about hinge 38. As best seen in FIG. 2, a set screw 50 is provided in body portion 48 to provide an adjustable spring bias by spring 51 against release 32.

Figure 3:
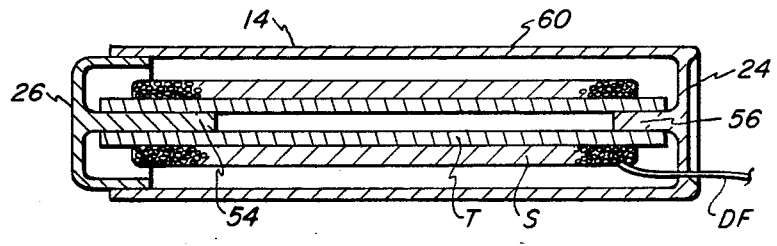
FIG. 3 is a section view through arrows 3—3 in FIG. 1.

Referring to FIG. 3, the refillable dental floss container 14 includes removeable cap 26 mateably engagable into housing 60 so that dental floss spool S may be inserted therein. Tube T on which the spool S is wrapped is typically hollow, and is therefore rotatably engageable over post 56 which is integral to the closed end 24 of housing 60. After so mounting the tube T, the removeable cap 26, including post 54, is installed in the opposite end of tube T and releasably secured into the open end of the dental floss container 14 as shown. By this means, the replaceable spool of floss S is held for easy rotation within the dental floss container 14 and the free end of the dental floss DF may be fed out of aperture 74 as previously discussed.

Figure 5:
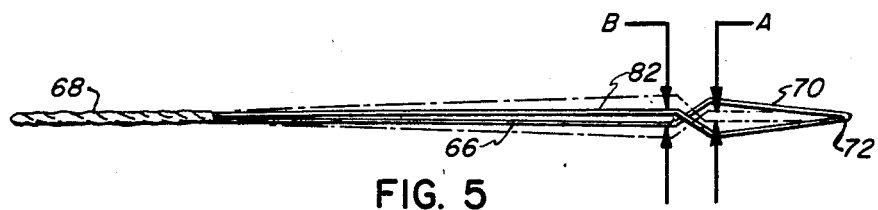
FIG. 5 is a top plan view of the separate floss feeder.

Referring to FIG. 5, a separate floss feeder 66 may be provided. This floss feeder 66 is fabricated of a single length of thin piano wire and has a pointed feeder eyelet 70 formed at one end as shown. Both ends of the length of piano wire are secured back against themselves at 68 to provide finger grasping means. This floss feeder 66 is provided to facilitate the routing of the dental floss DF out of aperature 74 and back into aperature 76 and exiting the aperature 58 in the removeable cap 26.

The floss feeder 66 includes a unique shape in the feeder eyelet 70 such that, after the dental floss DF has been passed through the pointed end 72 of the feeder eyelet 70, the resilient piano wire allows the feeder eyelet 70 to be reduced in size by side pressure thereapplied as that portion is passed through the aperatures 74, 76, and 58 down to dimension A. After the feeder eyelet 78 is pass through these apertures, it then returns to its normal shape as shown in solid lines so that the mid-portion 82 resumes its normal configuration and width dimension with B, thus allowing mid-portion 82 to also pass through the aperatures.

The body, floss lock bar and dental floss container are perferrably molded of plastic; but may be fabricated of other suitable material and processes.

While the instant invention has been shown and described herein in what is conceived to be the most practical and preferred embodiment, it is recognized that departures may be made therefrom within the scope of this invention, which is therefore not to be limited to the details disclosed herein, but is to be accorded the full scope of the claims so as to embrace any and all equivalent apparatus and articles.

What is claimed is:

1. A dental floss holder comprising:

an elongated main body having a top and bottom surface and a pair of extending spaced-apart opposing forks at one end and a refillable dental floss container disposed at the opposite end;

a floss lock bar pivotally connected at one end to a mid-portion of said top surface, the axis of said pivotal attachment generally transverse to said body;

each said fork having an eyelet at its distal end for receiving dental floss;

the lower surface of said floss lock bar having at least one protruding transversely disposed rib which is mateably receivable into a floss locking cavity in said body top surface when said floss lock bar is in a closed position;

said floss lock bar having a spring catch at its free end to releasably cooperate with a spring biased release pivotally mounted on said body top surface to hold said floss lock in a closed position;

the length of dental floss routable from a first aperture in a closed end of said dental floss container, between said rib and said cavity, along the length of one said fork and passing through each said fork eyelet such that the length of dental floss transversely spans and is held between said fork distal ends, then passing back along the length of the other said fork, between said rib and said cavity into a second aperture in said floss container closed end and exiting a third aperture in a removable cap of said floss container;

the outer surface of said removeable cap having a dental floss holder and cutter;

said rib and said cavity adapted to both tension and retain the so-routed dental floss when said floss lock bar is in the closed position.

2. A dental floss holder as set forth in claim 1, further comprising:

at least one additional pair of said mating rib and cavity for improved tensioning and retention of the so-routed dental floss.

3. A dental floss holder as set forth in claim 2, further comprising:

a pair of guides adjacent said floss lock bar and extending upwardly from said body top surface for assisting in positioning and retaining the dental floss between said mating ribs and cavities.

4. A dental floss holder as set forth in claim 3, further comprising:

adjustable tension means for varying the spring bias of said release against said spring catch;

said adjustable tension means mounted in said body adjacent the base of said forks.

5. A dental floss holder as set forth in claim 1, further comprising:

an elongated floss feeder for feeding dental floss through said first, second and third apertures.

6. A dental floss holder as set forth in claim 5, wherein:

said floss feeder is fabricated of a length of thin resilient wire having a finger grip portion at one end and a wedge-shaped feeder eyelet at the other end;

said feeder eyelet forming an opening through which the dental floss may be inserted;

said feeder eyelet adapted to be compressively narrowed to pass through said first, second and third aperture;

a mid-portion of said floss feeder sufficiently narrow when said feeder eyelet is in its free contour to pass through said first, second and third apertures.

* * * * *